United States Patent [19]
Unhoch et al.

[11] Patent Number: 5,668,084
[45] Date of Patent: Sep. 16, 1997

[54] POLYHEXAMETHYLENE BIGUANIDE AND SURFACTANT COMPOSITION AND METHOD FOR PREVENTING WATERLINE RESIDUE

[75] Inventors: Michael J. Unhoch, Wilmington, Del.; George D. Stratton, Oxford, Pa.

[73] Assignee: Zeneca Inc., Wilmington, Del.

[21] Appl. No.: 509,908

[22] Filed: Aug. 1, 1995

[51] Int. Cl.$^6$ .................... A01N 25/32; A01N 33/12; A01N 47/44

[52] U.S. Cl. .................................................. 504/158

[58] Field of Search ........................... 504/151, 153, 504/158, 159

[56] References Cited

U.S. PATENT DOCUMENTS

| | | | |
|---|---|---|---|
| 2,990,425 | 6/1961 | Senior | 260/501 |
| 3,142,615 | 7/1964 | Wehner | 167/22 |
| 3,183,230 | 5/1965 | Shapiro et al. | 260/244 |
| 3,222,398 | 12/1965 | Brown | 260/565 |
| 3,617,570 | 11/1971 | Redmore | 210/54 |
| 3,960,745 | 6/1976 | Billany et al. | 252/106 |
| 4,014,676 | 3/1977 | Carter et al. | 71/67 |
| 4,253,971 | 3/1981 | MacLeod et al. | 210/759 |
| 4,558,159 | 12/1985 | McCoy et al. | 564/233 |
| 4,661,523 | 4/1987 | Disch et al. | 514/635 |
| 4,758,595 | 7/1988 | Ogunbiyi et al. | 514/635 |
| 4,820,352 | 4/1989 | Riedhammer et al. | 134/30 |
| 5,096,607 | 3/1992 | Mowrey-McKee et al. | 252/106 |
| 5,223,149 | 6/1993 | Antelman | 210/764 |
| 5,356,555 | 10/1994 | Huth et al. | 252/106 |
| 5,508,250 | 4/1996 | Miller et al. | 504/158 |

FOREIGN PATENT DOCUMENTS

| | | |
|---|---|---|
| 0 542 199 A1 | 5/1993 | European Pat. Off. . |
| WO 93/16593 | 9/1993 | WIPO . |

*Primary Examiner*—S. Mark Clardy
*Attorney, Agent, or Firm*—Panitch Schwarze Jacobs & Nadel, P.C.

[57] ABSTRACT

A water treatment method for controlling the growth of algae, fungi and bacteria and the formation of a waterline residue in recreational and industrial water supplies containing turbulent water utilizes a composition containing a polyhexamethylene biguanide compound and a surfactant. The water treatment method and composition containing the biguanide compound and surfactant are particularly useful for treating recreational water supplies like spas and swimming pools containing turbulent water, such as aerated water.

33 Claims, No Drawings

POLYHEXAMETHYLENE BIGUANIDE AND SURFACTANT COMPOSITION AND METHOD FOR PREVENTING WATERLINE RESIDUE

FIELD OF THE INVENTION

The present invention relates to the treatment of water with compositions containing a biguanide compound.

BACKGROUND OF THE INVENTION

The treatment of industrial and recreational water supplies to control the growth of algae, fungi, bacteria and other pathogenic microorganisms is well-known. A traditional sanitizing method of treating such water is by chlorination. Environmental and end-user objections to chlorine have prompted the use of other compounds as replacements for chlorine in treating water supplies.

One alternative to the chlorination treatment of swimming pool water or other water supplies is the use of a linear polymeric biguanide, e.g., polyhexamethylene biguanide hydrochloride. U.S. Pat. No. 4,014,676 issued to Carter and U.S. Pat. No. 4,253,971 issued to MacLeod et al. describe the use of such biguanide compounds for swimming pool and/or cooling tower water treatment.

Guanidine compounds including biguanides, are well known and are used in a wide variety of applications, such as contact lens cleaners, skin cleansers, biocides, disinfectants, corrosion inhibitors, water clarifiers, etc., as described in U.S. Pat. No. 5,356,555 issued to Huth et al., U.S. Pat. No. 5,096,607 issued to Mowrey-McKee et al., U.S. Pat. No. 4,820,352 issued to Riedhammer et al., U.S. Pat. No. 4,758,595 issued to Ogunbiyi et al., U.S. Pat. No. 4,661,523 issued to Disch et al., U.S. Pat. No. 3,960,745 issued to Billany et al., U.S. Pat. No. 3,617,570 issued to Redmore, U.S. Pat. No. 3,222,398 issued to Brown, U.S. Pat. No. 3,183,230 issued to Shapiro et al., U.S. Pat. No. 3,142,615 issued to Wehner and U.S. Pat. No. 2,990,425 issued to Senior.

An object of the present invention is a water treatment method utilizing a polyhexamethylene biguanide-based composition that is particularly well-suited for treatment of turbulent water supplies, such as aerated water.

SUMMARY

In accordance with the present invention, a method for controlling the growth of algae, fungi and bacteria in water and the formation of a waterline residue is provided by introducing into a turbulent water supply an antimicrobial-effective amount of a polyhexamethylene biguanide compound and a water-soluble or water-dispersible surfactant.

While not wishing to be bound by any particular theory, it appears that the waterline residue in turbulent water systems treated with a polyhexamethylene biguanide is formed in part from a high molecular weight fraction of the biguanide compound, and it is believed that the high molecular weight fraction typically has an average molecular weight of at least about 2600. The water-soluble or water-dispersible surfactant in this invention is selected to control formation of the waterline residue.

The method is particularly well-suited for treating turbulent water, particularly aerated water, in recreational water supplies selected from the group consisting of spas, hot tubs, swim spas and swimming pools and industrial water supplies selected from the group consisting of cooling towers, industrial boilers and decorative fountains.

The biguanide compound is preferably a water-soluble salt of polyhexamethylene biguanide, most preferably polyhexamethylene biguanide hydrochloride.

The biguanide compound is desirably introduced into the water supply in an amount to yield a concentration in the water of from about 1 ppm to about 200 ppm, more preferably, from about 3 ppm to about 15 ppm in the water supply.

The water-soluble or water-dispersible surfactant is desirably cationic, nonionic or amphoteric. Particularly preferred surfactants include alkoxylated alkanolamides, di(hydrogenated tallow alkyl)-dimethyl quaternary ammonium chlorides, tallow alkyl benzyl dimethyl quaternary ammonium chlorides, hydrogenated tallow alkyl benzyl dimethyl quaternary ammonium chlorides, methyl bis(soya alkyl amidoethyl) 2-hydroxyethyl quaternary ammonium methyl sulfates, methyl bis(tallow alkyl amidoethyl) 2-hydroxyethyl quaternary ammonium methyl sulfates, $C_{12}$–$C_{18}$ ethoxylated propoxylated alcohols, $C_{16}$–$C_{18}$ fatty alcohol polyglycol ethers, alkylene oxide addition products, and polyoxypropylene-polyoxyethylene block copolymers with a hydrophile lipophile balance (HLB) of less than about 12.

The surfactant is introduced in an amount sufficient to control formation of a residue at the waterline of the turbulent and optionally aerated water supply. The surfactant desirably is introduced into the water supply in an amount to yield a concentration in the water supply of from about 0.1 ppm to about 50 ppm, more preferably, from about 1 ppm to about 20 ppm.

A composition containing the polyhexamethylene biguanide and surfactant may be used in this method, and an aqueous formulation thereof is preferred. Such formulations preferably contain from about 2 wt % to about 30 wt % biguanide compound and from about 0.01 wt % to about 25 wt % surfactant.

DESCRIPTION OF THE PREFERRED EMBODIMENTS

Guanidine-type compounds are generally these which contain the

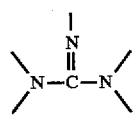

residue, such as biguanidine

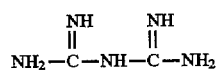

Linear polymeric biguanide in its free base form suitable for use in the present invention has a recurring polymer unit represented by the formula

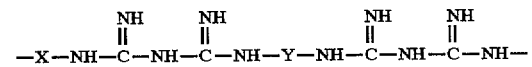

where X and Y represent bridging groups in which together the total number of carbon atoms directly interposed between the pairs of nitrogen atoms linked by X and Y is more than 9 and less than 17.

The bridging groups X and Y may consist of polymethylene chains, optionally interrupted by hetero atoms, for example, oxygen, sulphur or nitrogen. X and Y may also incorporate cyclic nuclei which may be saturated or unsaturated, in which case the number of carbon atoms directly interposed between the pairs of nitrogen atoms linked by X and Y is taken as including that segment of the cyclic group, or groups, which is the shortest.

The polymeric biguanides used in the present invention are preferably polyhexamethylene biguanides in which X and Y, in the above-noted formula for the recurring unit, both represent the —$(CH_2)_6$— group.

Polyhexamethylene biguanide, also referred to as poly(hexamethylene biguanide), PPLMB, or polyaminopropyl biguanide (PAPB), is preferably employed as a water-soluble salt. Such cationic salts may include water-soluble salts of common inorganic and organic acids such as chlorides, bromides, nitrates, sulfates, bisulfates, acetates, gluconates, and the like. Polyhexamethylene biguanide hydrochloride is most preferred for use in this invention.

Polyhexamethylene biguanide compounds are well known and are commercially available; e.g., Baquacil®, Vantocil® and BaquaSpa™ are trademarks for polyhexamethylene biguanide hydrochlorides marketed by Zeneca Inc., Wilmington, Del.

Polyhexamethylene biguanide compounds have recognized utility in the treatment of recreational and industrial/commercial water supplies. One problem in the water treatment industry, regardless of the sanitizer employed, is that a residue similar to a bathtub ring can form along the waterline, especially in aerated water systems. In spas, for example, use of polyhexamethylene biguanide can cause sticky residue or scum deposits along the waterline at the spa wall. The residue or scum is difficult to clean or remove and presents an aesthetically undesirable appearance in the spa.

The polyhexamethylene biguanides used in water treatment are typically polymeric mixtures. Commercially available polyhexamethylene biguanide hydrochlorides are usually polymer mixtures, with molecular weights that vary from about 1160 to about 3800, with the average molecular weight being about 2100. The high molecular weight fraction may be defined as that fraction having an average molecular weight of at least about 2600. Since the polymeric molecular weight distributions in polyhexamethylene biguanides will vary according to the manufacturing source, the threshold for the high molecular weight fraction could be lower than 2600 for some mixtures, e.g., 2400–2500 or less.

While not wishing to be bound by any particular theory, we believe that a high molecular weight fraction of the polymeric biguanide mixtures, typically having an average molecular weight of at least about 2600, is primarily responsible for the residue created during water treatment with polyhexamethylene biguanides. We believe that where turbulence of water occurs in the water supply, particularly where the water supply is aerated (a factor that contributes to turbulence), precipitation of this high molecular weight fraction is likely to result. This result can occur regardless of whether the water turbulence occurs generally throughout the water system or occurs only in a small portion of the water system, e.g., at a swimming pool skimmer. Under aerated conditions, the high molecular weight fraction is apparently drawn to the water's surface by interaction with air bubbles in the turbulent water and becomes concentrated as a residue on the water surface. This material containing the high molecular weight fraction of the polymeric biguanide compound is apparently then deposited along the water supply waterline as a residue or scum.

The formation of a residue when polyhexamethylene biguanide is employed in water treatment is most likely to occur when the water supply contains turbulent water, particularly aerated water. Such turbulent and optionally aerated water is typically contained in a confined water system such as may be found in spas, hot tubs, swim spas or swimming pools, and also in industrial and commercial water supplies such as cooling towers, boilers, decorative indoor and outdoor fountains and the like.

We have discovered that this residue problem can be controlled by introducing a surfactant into the water supply, where the surfactant is specifically selected to control waterline residue formation.

Suitable for use in the present invention are water-soluble or water-dispersible surfactants that effectively control formation of a waterline residue, by inhibiting or preventing formation of the waterline residue. Such water-soluble or water-dispersible surfactants may be selected from nonionic, cationic or amphoteric surfactants.

Since polyhexamethylene biguanide salts are cationic, anionic surfactants are best avoided since their use typically results in complexing or interreaction with biguanide that can lead to loss of the biguanide compound's antimicrobial activity. Compensation for any potential loss of antimicrobial activity can be made, however, by increasing the concentration of biguanide compound in the water supply.

Suitable surfactants desirably possess no objectionable or chemical odor and are low in toxicity, two attributes particularly important in treating recreational water supplies such as spas and swimming pools and commercial water supplies such as decorative fountains.

Suitable surfactants should desirably exhibit low foaming or controllable foaming characteristics, when utilized at the desired concentrations in the turbulent water supply. Among suitable surfactants, polyoxyethylene-derived surfactants such as poloxamers are especially preferred for use in this invention because of their low foaming characteristics. Other suitable surfactants, which are moderately or high foaming, may also be utilized in this invention, but use of an antifoaming agent or defoamer, preferably a silicone-based or siloxane-based antifoaming agent such as polydimethyl siloxane, may be desirable in conjunction with such surfactants, to maintain an acceptable, controlled level of foaming.

Suitable surfactants, especially nonionic surfactants, e.g., poloxamers, are typically characterized by having a hydrophile-lipophile balance below about 12. The hydrophile-lipophile balance (HLB) is a measure of the relative simultaneous attraction of a surfactant or emulsifier for each phase in a two-phase system, e.g., oil and water. HLB values between 1–10 ordinarily indicate lipophilic (hydrophobic) preference in a surfactant, and HLB values between 11–20 ordinarily indicate a hydrophilic preference.

While not wishing to be bound to a particular theory or mechanism, we believe that in aerated turbulent water systems, the air bubbles are the functional equivalent of the lipophilic (oil) phase. The effectiveness of suitable surfactants in this invention appears to be based at least in part on their ability to create a barrier on such air bubbles that inhibits the high molecular weight fraction of the polymeric biguanide mixture from becoming associated with the air bubbles. Consequently, surfactants with relatively low HLB values, i.e., neutral or more lipophilic surfactants having HLB values of less than about 12, appear to perform more effectively in controlling residue formation in the turbulent water.

Particularly preferred surfactants are alkoxylated alkanolamides such as Makon® NF-5 (Stepan Co., Northfield, Ill.); di(hydrogenated tallow alkyl)-dimethyl quaternary ammonium chlorides such as Arquad® 2HT-75 (Akzo Chemicals Inc., Chicago, Ill.); tallow alkyl benzyl dimethyl quaternary ammonium chloride such as Kemamine BQ-9742C (Witco Chemical Corp., Memphis, Tenn.) and hydrogenated tallow alkyl benzyl dimethyl quaternary ammonium chloride such as Kemamine Q-9702C (Witco Chemical Corp.); methyl bis(soya alkyl amidoethyl) 2-hydroxyethyl quaternary ammonium methyl sulfate such as Accosoft 750 (Stepan Co., Northfield, Ill.); methyl bis(tallow alkyl amidoethyl) 2-hydroxyethyl quaternary ammonium methyl sulfate such as Accosoft 501 (Stepan Co.); $C_{12}$–$C_{18}$ ethoxylated propoxylated alcohols such as Plurafac D-25 (BASF Corporation, Mt. Olive, N.J.); $C_{16}$–$C_{18}$ fatty alcohol polyglycol ethers such as Marlipal 1618/25 (Hüls AG, Marl, Germany); alkylene oxide addition products such as Marlox FK 64 (Hüls AG, Marl, Germany) and polyoxypropylene-polyoxyethylene block copolymers (poloxamers) with an HLB less than about 12 such as Pluronic® 25R4 (BASF Corporation).

Suitable surfactants may also be selected from the following categories of water-soluble or water-dispersible cationic and nonionic surfactants.

Cationic surfactants that are quaternary ammonium salts typified by the general formula

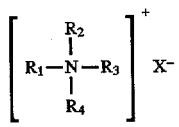

where $R_1$ is a mixed aliphatic radical derived from $C_8$–$C_{20}$ fatty acids or their hydrogenated analogs; $R_3$ is a mixed aliphatic radical derived from $C_8$–$C_{20}$ fatty acids or their hydrogehydrogenated analogs or an aryl radical; $R_2$ is an aliphatic hydrocarbon radical having 1–20 carbon atoms; and X is a monovalent anion or monovalent equivalent of a multivalent anion, e.g., halide, sulfate, nitrate, methylsulfate, acetate, borate, gluconate or other inorganic or common organic acid salt.

In the general formula, $R_1$ and $R_3$ are preferably $C_{14}$–$C_{18}$ fatty acids or their hydrogenated analogs, and X is preferably chloride or bromide.

Preferred quaternary ammonium salt surfactants having the above-noted general formula are as follows:

Compounds where $R_1$ and $R_3$ are hydrogenated tallow fatty acid alkyls (primarily stearyl ($C_{18}$ alkyls)), $R_2$ and $R_4$ are methyl groups, and X is chloride. Arquad® 2HT-75 quaternary salt (Akzo Chemicals Inc., Chicago, Ill.), a di(hydrogenated tallow alkyl)-dimethyl quaternary ammonium chloride, is exemplary.

Compounds where $R_1$ and $R_3$ are respectively hydrogenated tallow fatty acid alkyl and benzyl, $R_2$ and $R_4$ are methyl groups, and X is chloride. Kemamine® 9742C quaternary salt (Witco Chemical Corp., Memphis, Tenn.), a dimethyl tallow alkyl benzyl quaternary ammonium chloride, is exemplary.

Compounds where $R_1$ and $R_3$ are coconut fatty acid alkyls (primarily $C_{12}$–$C_{16}$ alkyls); $R_2$ and $R_4$ are methyl groups and X is chloride. Arquad® 2C-75 quaternary salt (Akzo Chemicals Inc., Chicago, Ill.), a dicocoalkyl dimethyl quaternary ammonium chloride, is exemplary.

Suitable cationic surfactants also include quaternary ammonium salts of the general formula:

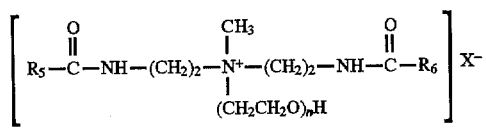

where $R_5$ and $R_6$ are the same or different mixed aliphatic radicals derived from $C_8$–$C_{20}$ (preferably $C_{14}$–$C_{20}$) fatty acids or their hydrogenated analogs; X is a monovalent anion or monovalent equivalent of a multivalent anion, preferably a halide, sulfate, nitrate, methyl sulfate, acetate, borate, gluconate or the like; and n is an integer of from 1–30, preferably 1–10. Accosoft® 750 quaternary salt (Stepan Co., Northfield, Ill.), a methyl bis(soya alkyl amidoethyl) 2-hydroxyethyl quaternary ammonium methylsulfate, and Accosoft® 501 quaternary salt (Stepan Co., Northfield, Ill.), a methyl bis(tallow alkyl amidoethyl) -2-hydroxyethyl ammonium methyl sulfate, are exemplary.

Suitable surfactants include amines having the general formulas:

where $R_7$ is a mixed aliphatic radical preferably derived from a $C_8$–$C_{20}$ fatty acid or its hydrogenated analog; and m is an integer from 0–50.

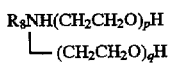

where $R_8$ is a mixed aliphatic radical, preferably derived from a $C_8$–$C_{20}$ fatty acid or its hydrogenated analog; and p and q are integers of between 1–50 whose sum is in the range of 2–50.

Suitable surfactants also include polyalkylene and polyoxyalkylene glycols, polyoxypropylene-polyoxyethylene block copolymers (poloxamers), polyoxypropylene polymer derivatives and polyoxyethylene polymer derivatives, including those with the following general formulas:

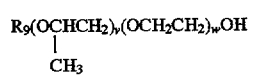

where $R_9$ is a mixed aliphatic hydrocarbon, preferably derived from a $C_8$–$C_{20}$ fatty acid or its hydrogenated analog; v is an integer of from 0–50, preferably 6–11; and w is an integer of from 0–10, preferably 0–4.

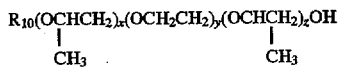

where $R_{10}$ is a mixed aliphatic hydrocarbon, preferably derived from a $C_8$–$C_{20}$ fatty acid or its hydrogenated analog; and x, y and z are integers with x and z being 0–30, preferably 3–20 and more preferably about 1–18, and y being 0–40, preferably 11–34.

In the above-noted general formulas, the R groups that are mixed aliphatic hydrocarbon radicals include alkyl groups that are alike or different, substituted or unsubstituted, linear or branched, cyclic or acyclic, including mixtures derived from natural sources. These can include mixed aliphatic hydrocarbon radicals that are derived from fatty acids or their hydrogenated (fully or partially) analogs and include those obtained from animal, plant, and marine fat/oil sources, e.g., tallow, soybean oil, coconut oil, palm oil, palm kernel oil, fish oil, rapeseed oil, and tall oil; tallow, soybean and tall oil are preferred sources. Fatty acid aliphatics derived from petroleum sources, preferably $C_{10}$–$C_{18}$ and more preferably $C_{14}$–$C_{18}$ aliphatics, can also be used.

The method and composition of this invention are directed to treatment of turbulent water supplies, such as aerated water supplies. It should be apparent from the disclosures herein that water supplies that are sparged with gases other than air, e.g., oxygen, nitrogen, etc., are also well suited for use with this invention.

The polyhexamethylene biguanide compound and surfactant may be introduced into the water supply in a variety of different ways, using conventional, well-known techniques.

The two compounds may be introduced separately or together, as a formulated composition, which may optionally contain other ingredients. The addition may be continuous, using metering equipment, or more preferably, may be intermittent, with dosages being introduced either at periodic intervals or on an as-needed basis.

The polyhexamethylene biguanide compound, especially the preferred hydrochloride salt, is desirably added to the water being treated in the form of an aqueous solution, preferably containing from about 2 wt % to about 30 wt % of the biguanide compound. Aqueous solutions of the biguanide containing from about 5 wt % to about 25 wt % biguanide compound are more preferred, with about 20 wt % being an especially preferred concentration for swimming pools and about 5 wt % to about 20 wt % being an especially preferred concentration range for spas.

Sufficient biguanide should be introduced into the turbulent water supply to provide an amount whose concentration in the water is effective to control the growth of algae, fungi and bacteria and other pathogenic microorganisms in the water (an "antimicrobial-effective amount"). The aqueous concentration of polyhexamethylene biguanide compound in the treated water is preferably within a range of about 1 ppm to about 200 ppm, and more preferably, within a range of about 3 ppm to about 15 ppm (all ppm values in this disclosure are wt./wt. basis unless noted otherwise).

For pools and spas, the concentration of the biguanide compound in the turbulent water is most preferably maintained within the range of about 6 ppm to about 10 ppm.

The surfactant, if added separately from the biguanide compound, is preferably introduced as an aqueous solution or suspension, containing from about 2 wt % to about 97 wt % surfactant, more preferably, about 5 wt % to about 30 wt % surfactant. The precise concentration of surfactant utilized will likely depend on the specific surfactant selected and its physical characteristics.

The concentration of surfactant in aqueous formulations also containing the biguanide compound should be in the range of about 0.01 wt % to about 25 wt %, more preferably, in the range of about 0.05 wt % to about 10 wt %. For swimming pools and spas, such aqueous formulations desirably should contain about 0.1 wt % to about 5 wt % surfactant (preferably with about 20 wt % biguanide compound for swimming pools and about 5 wt % to about 20 wt % biguanide compound for spas).

The amount of surfactant introduced into the turbulent water supply should be adjusted to be sufficient to control formation of the residue at the waterline of the turbulent water supply. Visual inspection is normally adequate for determining whether the amount of surfactant being used is insufficient for preventing or controlling formation of the residue or scum along the waterline.

The amount of surfactant introduced into the turbulent water supply for controlling residue formation will ordinarily be an amount sufficient to yield a surfactant concentration in the water within a range of about 0.1 ppm to about 50 ppm, more preferably, within a range of about 1 ppm to about 20 ppm. For swimming pools and spas, the surfactant concentration in the water is desirably maintained in a range of about 2 ppm to about 15 ppm, and more preferably, in a range of about 3 ppm to about 10 ppm.

The invention is illustrated further by the following specific, nonlimiting Examples.

EXAMPLE 1

A 300 gallon recreational spa that had previously exhibited waterline residue problems when the water was treated with polyhexamethylene biguanide hydrochloride alone (without any surfactant) was utilized in this Example for a long-term evaluation of three different surfactants, used individually in combination with polyhexamethylene biguanide.

The three surfactants were Arquad® 2HT-75 quaternary salt, a di(hydrogenated tallow alkyl)-dimethyl quaternary ammonium chloride (Akzo Chemical Co.); Makon® NF-5 alkoxylated alkanolamide (Stepan Co.); and Pluronic® 25R4 poloxamer, a polyoxypropylene-polyoxyethylene block copolymer with a hydrophile lipophile balance in the range of 7–12 (BASF Corp.).

The spa was filled with tap water, and the water balance was adjusted to pH 7.2–7.8, total alkalinity of 80–120 ppm, and a calcium hardness of 200–400 ppm. The spa water was warmed and maintained at a temperature of about 100°–104° F. These values were maintained throughout the test period, approximately two months for each surfactant.

The water in the spa was then treated by the initial addition of polyhexamethylene biguanide hydrochloride (PHMB) in a 20 wt % aqueous solution, to provide a concentration of 10 ppm PHMB in the water. The water was also treated with separate additions ethylenediaminetetraacetic acid, as a chelating agent for metals and minerals (to prevent water discoloration, staining and mineral deposits), and aqueous hydrogen peroxide as a shock treatment (for oxidizing organics to control their buildup). The spa water was circulated using the spa jets for 15 minutes between addition of each of these chemicals.

Throughout the test period of approximately two months (for each surfactant) the PHMB in the spa water was maintained at a concentration of about 6–10 ppm. Ethylenediaminetetraacetic acid and aqueous hydrogen peroxide were also added weekly.

During the course of the separate studies with each of the three surfactants, as described below, the spa was subject to normal recreational use. Whenever the spa was in actual use, the spa water was circulated using the spa jets and air was injected into the spa using the spa blower to aerate the recirculated water supply. Formation of waterline residue deposits was monitored by visual observation.

The three surfactants were each used in separate long-term studies. The Arquad® 2HT-75 surfactant was initially introduced as a dilute aqueous dispersion in an amount to provide a concentration of 8 ppm in the spa water. Subsequently, this surfactant was added periodically, on an as-needed basis (typically about once every 6 days), as waterline residue deposits were observed to begin to be formed, in an amount sufficient to provide a concentration of 2 ppm in the spa water.

In a separate study, the Makon® NF-5 surfactant was initially added as an aqueous solution in an amount sufficient to provide a concentration of 10 ppm in the spa water. Subsequently, this surfactant was added periodically, on an as-needed basis (typically about once every 3 days) when waterline residue deposits began to form, in an amount sufficient to provide a concentration of 3 ppm in the water.

In the third study, Pluronic® 25R4 surfactant was initially introduced as an aqueous solution in an amount sufficient to provide a concentration of 10 ppm in the water. Subsequently, the surfactant was added on an as-needed basis (about once every 12 days) when waterline residue deposits began to form, in an amount sufficient to provide a concentration of 10 ppm in the water.

With each of the three surfactants, this treatment methodology provided adequate control of the residue formation; the formation of waterline residue deposits was eliminated immediately after such periodic surfactant treatments.

In each of these studies with the three surfactants, water clarity remained satisfactory and no problems were encountered with surfactant solubility in the spa water.

Each of the three surfactants studied provided good control of the residue formation and eliminated the waterline residue deposits, notwithstanding that polyhexamethylene biguanide hydrochloride was used for water treatment of the aerated spa water.

EXAMPLE 2

In this Example, numerous surfactant compounds, including compounds with surfactant-like activity, were each screened in recreational spas over a three hour period, to evaluate their efficacy in controlling formation of waterline residue deposits.

The 250-gallon spas were filled with tap water that was chemically balanced to the same parameter values employed in Example 1 for pH, total alkalinity, calcium hardness and water temperature. Prior to each screening of a specific compound, the spa water was treated with polyhexamethylene biguanide hydrochloride, ethylenediaminetetraacetic acid and hydrogen peroxide, identically as described for Example 1.

An amount of each surfactant or other compound studied was then introduced into the spa water to provide a concentration of 15 ppm in the water. This concentration of surfactant in the water was selected for screening purposes only, even though for some surfactants (such as the three employed in Example 1) it represented a much higher use level than optimally required for effective control and may have also caused higher levels of surfactant-induced foaming than would ordinarily be encountered at lower dosage levels. For surfactants in this screening that exhibited excessive foaming, an antifoam (polydimethyl siloxane) was added in an amount sufficient to provide a concentration of 0.5 ppm in the water.

During the three-hour evaluation period after each surfactant was added, the spa water was circulated using the spa jets and air was injected into the spa water using the spa blowers to aerate the water. During this period, the spas were monitored visually for residue formation and for foaming.

In this study, only those surfactant compounds that were water-soluble or water-dispersible and that were free of highly objectionable odors were subjected to the screening study. The results of the study are summarized in Table 1 below. The Table identifies each surfactant compound (i) by trademark name and product identification number, (ii) by the compound's chemical designation or classification and (iii) by surfactant ionicity, where known. Levels of foaming and residue formation are noted as none, slight, moderate or heavy, with heavy residue formation being deemed unacceptable for a candidate surfactant to be utilized in this invention.

The study results in Table 1 for the numerous surfactants evaluated, over four dozen of which were included in the study, indicates the range and types of surfactants and other functionally equivalent compounds that are suitable for use in this invention.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

TABLE 1

SCREENING EVALUATION RESULTS

| Product | Compound | Ionicity | Foam | Residue |
|---|---|---|---|---|
| CONTROL | (PHMB Only - No Surfactant) | NA | Moderate | Heavy |
| Arquad 2 HT-75 | Di(hydrogenated tallow alkyl) - dimethyl quaternary ammonium chloride | Cationic | Heavy | None |
| Arquad 2Ht-75 PG | Di(hydrogenated tallow alkyl) - dimethyl quaternary ammonium chloride | Cationic | Heavy | Slight |
| Arquad 2C-75 | Dicoco alkyl dimethyl quaternary ammonium chloride | Cationic | Heavy | Moderate |
| Accosoft 750 | Methyl bis(tallow alkyl amidoethyl) 2-hydroxyethyl ammonium methyl sulfate | Cationic | Slight | Very slight |
| Accosoft 501 | Methyl bis(tallow alkyl amido ethyl) 2-hydroxyethyl ammonium methyl sulfate | Cationic | Moderate | Very slight |
| Accosoft 808 | Tallow imidazoline quaternary ammonium salt | Cationic | Heavy | Very slight |
| Kemamine BQ-9742C | Dimethyl tallow alkyl benzyl quaternary ammonium chloride | Cationic | Moderate | Moderate |
| Kemamine Q-9702C | Dimethyl hydrogenated tallow alkyl benzyl quaternary ammonium chloride | Cationic | Moderate | None |
| WSCP | Poly[oxyethylene(dimethyl-iminio)ethylene-(dimethyliminio)-ethylene | Cationic | Slight | Very slight |

TABLE 1-continued

SCREENING EVALUATION RESULTS

| Product | Compound | Ionicity | Foam | Residue |
|---|---|---|---|---|
| | dichloride | | | |
| Ammonyx CETAC-30 | Cetyl trimethyl ammonium chloride | Cationic | Heavy | Moderate |
| Ammonyx-4 | Quaternary amine hydrochloride | Cationic | None | Slight |
| Chemstat 106G/90 | (Bis(2-hydroxyethyl) octyl methyl ammonium para-toluensulfonate | Cationic | None | Slight |
| Rhodameen T-30/90 | Ethoxylates of primary tallow amines | Cationic | Slight | Moderate |
| Aerosol C-61 | Ethoxylated octadeclamine-octadecyl guanidine | Cationic | Heavy | Heavy |
| Biodex Enzyme | Proprietary enzyme and surfactant | Nonionic | Moderate | Slight |
| Amersil ME-358 | Organosilicone fluid | Nonionic | Slight | Slight |
| Arcol PPG-425 Polyol | Polypropylene glycol | Nonionic | Moderate | Moderate |
| Arcol PPG-1025 Polyol | Polypropylene glycol | Nonionic | Slight | Moderate |
| Pluronic 25R4 (HLB 7-12) | Polyoxypropylene-polyoxyethylene block copolymer | Nonionic | Moderate | None |
| Pluronic 25R2 (HLB 2-7) | Polyoxypropylene-polyoxyethylene block copolymer | Nonionic | Slight | None |
| Pluracol W3520N | Polyoxypropylene-polyoxyethylene block copolymer | Nonionic | Slight | Moderate |
| Pluronic L-61 (HLB 1-7) | Polyoxypropylene-polyoxyethylene glycol | Nonionic | None | None |
| Drewplus Y-250 | Polypropylene glycol | Nonionic | Slight | Slight |
| Drewplus ED 795 | Polyalkylene glycol | Nonionic | Slight | None |
| Ethox MA-8 | Ethoxylated fatty acid | Nonionic | Slight | None |
| Macol 2LF | Polyoxyalkylene Glycol | Nonionic | Slight | None |
| Makon NF-5 | Alkoxylated Alkanolamide | Nonionic | Low | None |
| Makon NF 12 | Polyalkoxylated aliphatic base | Nonionic | None | None |
| Plurafac D-25 | C12–C18 ethoxylated propoxylated alcohol | Nonionic | None | None |
| Hetoxamine T-15 | Tallowamine POE-15 | Nonionic | Heavy | None |
| Hetoxamine T-20 | Tallowamine POE-20 | Nonionic | Heavy | None |
| Hetoxamine T-50 | Tallowamine PEG-50 | Nonionic | Heavy | None |
| Amway LOC | N-bis(hydroxethyl)-cocoamides C12–C15 ethoxylated alcohols | Nonionic | Heavy | Slight |
| Pluronic P-65 (HLB 12-18) | Block copolymer of ethylene and propylene oxide | Nonionic | Heavy | Moderate |
| Antarox L-61 | Alkoxylated glycols (block copolymers) polyoxymer | Nonionic | Slight | Slight |
| Foam Blast SPD | Organic defoamer | Nonionic | Slight | Moderate |
| Trycol 5882 | Ethoxylated fatty alcohol | Nonionic | Slight | None |
| Genapol 26-L-60N | C12–C18 linear ethoxylated alcohol | Nonionic | Heavy | None |
| Marlipal 1618/25 | C16–C18 Fatty alcohol polyglycol ether | Nonionic | Heavy | None |
| Softigen 767 | Ethoxylated mono/diglyceride of capric/caprylic acids | Nonionic | None | Moderate |
| Marlowet OTS | Carboxylic acid polyglycol ester | Nonionic | None | Moderate |
| Marlox MO 154 | Fatty alcohol alkylene oxide addition product | Nonionic | None | Slight |
| Marlox FK 64 | Alkylene oxide addition product | Nonionic | Slight | None |
| Marlowet LVS | Carboxylic acid polyglycol ester | Nonionic | None | Slight |
| Pluronic 10R5 (HLB 12-18) | Block copolymer of ethylene and propylene oxide | Nonionic | Heavy | Heavy |
| Ampholyt JA140 | Proprietary compound | Nonionic | None | Heavy |
| Pluronic L-64 (HLB 12-18) | Block copolymer of ethylene and propylene oxide | Nonionic | Moderate | Heavy |
| Natural Chemistry BS-5 | Enzyme (30%) nonionic surfactant (70%) | Nonionic | Moderate | Heavy |
| Biosoft TA-2 | Tallowamine ethoxylate (2 moles) | Amphoteric | None | Very slight |
| Armak 1703 | Proprietary amino compound | Not known | Slight | None |
| Mackamine C-8 | oxtylamine oxide | Not known | NA | Slight |
| Monateric CHEM 38 | Substituted imidazoline derivatives | Not known | Slight | Heavy |
| Tego Antifoam 2-87 | Organo-modified polysiloxanes | NA | Slight | None |
| Tego Antifoam 1488 | Organo-modified polysiloxanes | NA | Slight | Moderate |
| Tegopren 5873 | Silicone | NA | Slight | None |
| BSPA Foam Disperser | Polydimethyl Siloxane | NA | Moderate | Moderate |

What is claimed is:

1. A method for controlling the growth of algae, fungi and bacteria in water susceptible to formation of a waterline residue which comprises introducing into a turbulent water supply an antimicrobial-effective amount of a polyhexamethylene biguanide compound and a water-soluble or water-dispersible surfactant said surfactant being introduced in an amount sufficient to control formation of a residue at the waterline of the turbulent water supply.

2. The method of claim 1 wherein the turbulent water supply is selected from the group consisting of spas, hot tubs, swim spas, swimming pools, cooling towers, industrial boilers and decorative fountains.

3. The method of claim 1 wherein the turbulent water supply is also aerated.

4. The method of claim 1 wherein the surfactant is selected to control formation of a waterline residue containing a high molecular weight fraction of the biguanide compound.

5. The method of claim 1 wherein the biguanide compound is polyhexamethylene biguanide hydrochloride.

6. The method of claim 1 wherein the biguanide compound is introduced into the turbulent water supply in an amount to yield a concentration in the water of from about 1 ppm to about 200 ppm.

7. The method of claim 1 wherein the biguanide compound is introduced into the turbulent water supply in an amount to yield a concentration in the water of from about 3 ppm to about 15 ppm.

8. The method of claim 1 wherein the surfactant is a nonionic surfactant with a lipophile hydrophile balance below about 12.

9. The method of claim 1 wherein the surfactant is selected from the group consisting of alkoxylated alkanolamides, polyoxypropylene-polyoxypropylene block copolymers with a hydrophile-lipophile balance below about 12, $C_{12}$–$C_{18}$ ethoxylated propoxylated alcohols, $C_{16}$–$C_{18}$ fatty alcohol polyglycol ethers, alkylene oxide addition products, and methyl bis(soya alkyl amidoethyl) 2-hydroxyethyl quaternary ammonium methyl sulfate and methyl bis(tallow alkyl amidoethyl) 2-hydroxyethyl quaternary ammonium methyl sulfate.

10. The method of claim 1 wherein the surfactant is introduced into the turbulent water supply in an amount to yield a concentration in the water of from about 0.1 ppm to about 50 ppm.

11. The method of claim 1 wherein the surfactant is introduced into the turbulent water supply in an amount to yield a concentration in the water of from about 1 ppm to about 20 ppm.

12. The method of claim 1 which further comprises introducing the polyhexamethylene biguanide compound and surfactant together, as an aqueous formulation thereof, into the turbulent water supply.

13. The method of claim 12 wherein the concentration of biguanide compound in the aqueous formulation is from about 2 wt % to 30 wt % and the surfactant concentration in the aqueous formulation is from about 0.01 wt % to about 25 wt %.

14. The method of claim 12 wherein the concentration of biguanide compound in the aqueous formulation is from about 5 wt % to 25 wt % and the surfactant concentration in the aqueous formulation is from about 0.05 wt % to about 10 wt %.

15. A method for controlling the growth of algae, fungi and bacteria in water susceptible to formation of a waterline residue which comprises introducing into a turbulent water supply an antimicrobial-effective amount of a polyhexamethylene biguanide compound and a water-soluble or water-dispersible surfactant selected from the group consisting of di(hydrogenated tallow alkyl)-dimethyl quaternary ammonium chloride, tallow alkyl benzyl dimethyl quaternary ammonium chloride and hydrogenated tallow alkyl benzyl dimethyl quaternary ammonium chloride, said surfactant being introduced in an amount sufficient to control formation of a residue at the waterline of the turbulent water supply.

16. The method of claim 15 wherein the turbulent water supply is selected from the group consisting of spas, hot tubs, swim spas, swimming pools, cooling towers, industrial boilers and decorative fountains.

17. The method of claim 15 wherein the turbulent water supply is also aerated.

18. The method claim 15 wherein the biguanide compound is polyhexamethylene biguanide hydrochloride.

19. The method of claim 15 wherein the biguanide compound is introduced into the turbulent water supply in an amount to yield a concentration in the water of from about 3 ppm to about 15 ppm.

20. The method of claim 15 wherein the surfactant is introduced into the turbulent water supply in an amount to yield a concentration in the water of from about 1 ppm to about 20 ppm.

21. The method of claim 15 which further comprises introducing the polyhexamethylene biguanide compound and surfactant together, as an aqueous formulation thereof, into the turbulent water supply.

22. The method of claim 21 wherein the concentration of biguanide compound in the aqueous formulation is from about 2 wt % to about 30 wt % and the surfactant concentration in the aqueous formulation is from about 0.01 wt % to about 25 wt %.

23. The method of claim 21 wherein the concentration of biguanide compound in the aqueous formulation is from about 5 wt % to about 25 wt % and the surfactant concentration in the aqueous formulation is from about 0.05 wt % to about 10 wt %.

24. A composition for controlling the growth of algae, fungi and bacteria and the formation of a waterline residue in a turbulent water supply comprising an aqueous formulation of a polyhexamethylene biguanide compound and a water-soluble or water-dispersible suffactant. said surfactant being selected from the group consisting of alkoxylated alkanolamides. polyoxypropylene-polyoxypropylene block copolymers with a hydrophile-lipophile balance below about 12, $C_{12}$–$C_{18}$ ethoxylated propoxylated alcohols. $C_{16}$–$C_{18}$ fatty alcohol polyglyc91 ethers, alkylene oxide addition products. methyl bis(soya alkyl amidoethyl) 2-hydroxyethyl quaternary ammonium methyl sulfate and methyl bis(tallow alkyl amidoethyl) 2-hydroxyethyl quaternary ammonium mthyl sulfate, wherein the concentration of biguanide compound is from about 2 wt % to 30 wt % and the surfactant concentration is from about 0.01 wt % to about 25 wt %.

25. The composition of claim 24 wherein the surfactant is present in an amount sufficient to control formation of a waterline residue containing a high molecular weight fraction of the biguanide compound.

26. The composition of claim 24 wherein the biguanide compound is polyhexamethylene biguanide hydrochloride.

27. The composition of claim 24 wherein the surfactant is a nonionic surfactant with a lipophile hydrophile balance below about 12.

28. The composition of claim 24 wherein the concentration of biguanide compound is from about 5 wt % to 25 wt % and the surfactant concentration is from about 0.05 wt % to about 10 wt %.

29. A composition for controlling the growth of algae, fungi and bacteria and the formation of a waterline residue in a turbulent water supply comprising a polyhexamethylene biguanide compound and a water-soluble or water-dispersible surfactant selected from the group consisting of di(hydrogenated tallow alkyl)-dimethyl quaternary ammonium chloride, tallow alkyl benzyl dimethyl quaternary ammonium chloride and hydrogenated tallow alkyl benzyl dimethyl quaternary ammonium chloride.

30. The composition of claim 29 wherein the biguanide compound is polyhexamethylene biguanide hydrochloride.

31. The composition of claim 29 which further comprises an aqueous formulation of the polyhexamethylene biguanide compound and surfactant.

32. The composition of claim 31 wherein the concentration of biguanide compound is from about 2 wt % to about 30 wt % and the surfactant concentration is from about 0.01 wt % to about 25 wt %.

33. The composition of claim 31 wherein the concentration of biguanide compound is from about 5 wt % to about 25 wt % and the surfactant concentration is from about 0.05 wt % to about 10 wt %.

* * * * *